United States Patent [19]

Mehl, Sr. et al.

[11] Patent Number: 5,470,332
[45] Date of Patent: Nov. 28, 1995

[54] SYSTEM FOR PERMANENT REMOVAL OF MULTIPLE HAIRS

[75] Inventors: Thomas L. Mehl, Sr., Rte. 1, 1015 Highway 337, Old Bronson Rd., Newberry, Fla. 32669; George W. Harris, Jr., Melbourne; Nardo Zaias, Miami Beach, both of Fla.

[73] Assignee: Thomas L. Mehl, Sr., Newberry, Fla.

[21] Appl. No.: 176,561

[22] Filed: Dec. 30, 1993

Related U.S. Application Data

[63] Continuation-in-part of Ser. No. 917,662, Jul. 20, 1992, abandoned, which is a continuation of Ser. No. 794,364, Nov. 13, 1991, abandoned, which is a continuation of Ser. No. 454,622, Dec. 21, 1989, abandoned, and a continuation-in-part of Ser. No. 66,261, May 25, 1993, abandoned, which is a continuation-in-part of Ser. No. 929,750, Aug. 17, 1992, abandoned, which is a continuation-in-part of Ser. No. 707,828, May 30, 1991, abandoned.

[51] Int. Cl.$^6$ .................................................. A61B 17/41
[52] U.S. Cl. ................................ 606/36; 606/43; 606/134
[58] Field of Search ..................... 606/32, 36, 43, 606/133, 134; 607/152

[56] References Cited

U.S. PATENT DOCUMENTS

| | | |
|---|---|---|
| 2,888,927 | 6/1959 | Fozard . |
| 4,033,350 | 7/1977 | Hoshi . |
| 4,174,714 | 11/1979 | Mehl . |
| 4,237,886 | 12/1980 | Sakurada et al. ............... 606/32 |
| 4,274,413 | 6/1981 | Hahn et al. . |
| 4,311,145 | 1/1982 | Esty et al. . |
| 4,317,450 | 3/1982 | Chalmers et al. . |
| 4,367,745 | 1/1983 | Welage ............................ 607/152 |
| 4,498,474 | 2/1985 | Chalmers et al. . |
| 5,026,369 | 6/1991 | Cole . |
| 5,049,148 | 9/1991 | Mehl . |
| 5,064,993 | 11/1991 | Hashimoto . |
| 5,133,712 | 7/1992 | McPherson . |
| 5,163,288 | 11/1992 | Doley . |

*Primary Examiner*—Lee S. Cohen
*Attorney, Agent, or Firm*—Shlesinger Arkwright & Garvey

[57] ABSTRACT

Multiple hair removal system includes an adhesive layer, a structural layer disposed adjacent the adhesive layer, and a conductive material. The conductive material functions to provide power from a power source to hairs to be treated that extend up through the adhesive layer and contact the conductive material. A method of removing multiple hairs and inhibiting future hair growth includes the steps of applying a conductive solution to the skin, pressing on an adhesive layer, applying power for a period of time sufficient to destroy the matrix area of the hair, and allowing the treated hair to either be removed immediately or to stay in the skin for a period of time sufficient for the chemical reaction induced at the matrix area to continue long enough to destroy the matrix area and prevent regrowth of the hair.

12 Claims, 4 Drawing Sheets

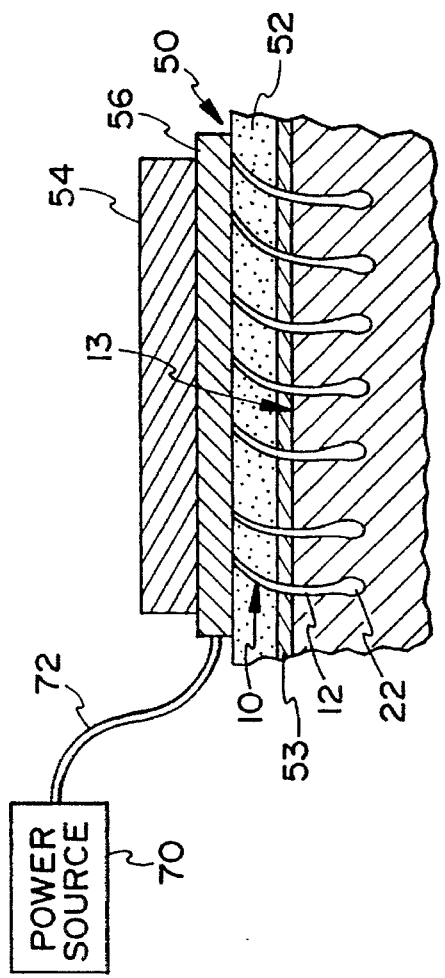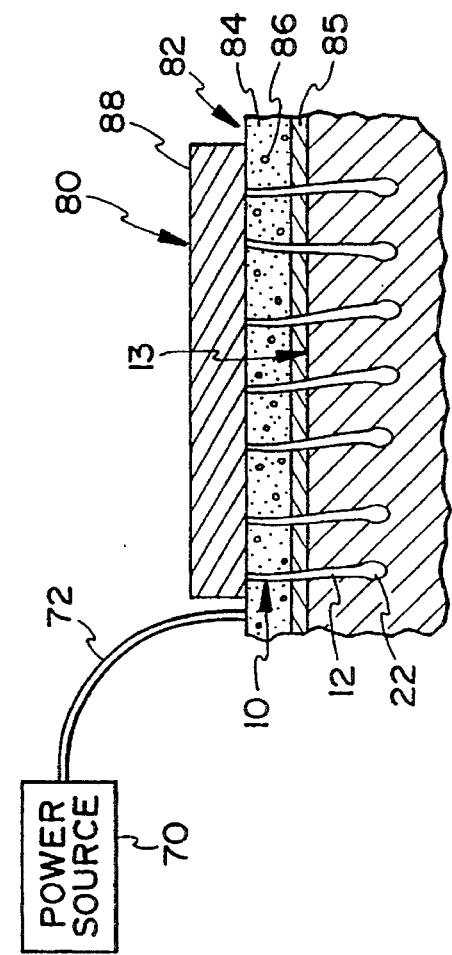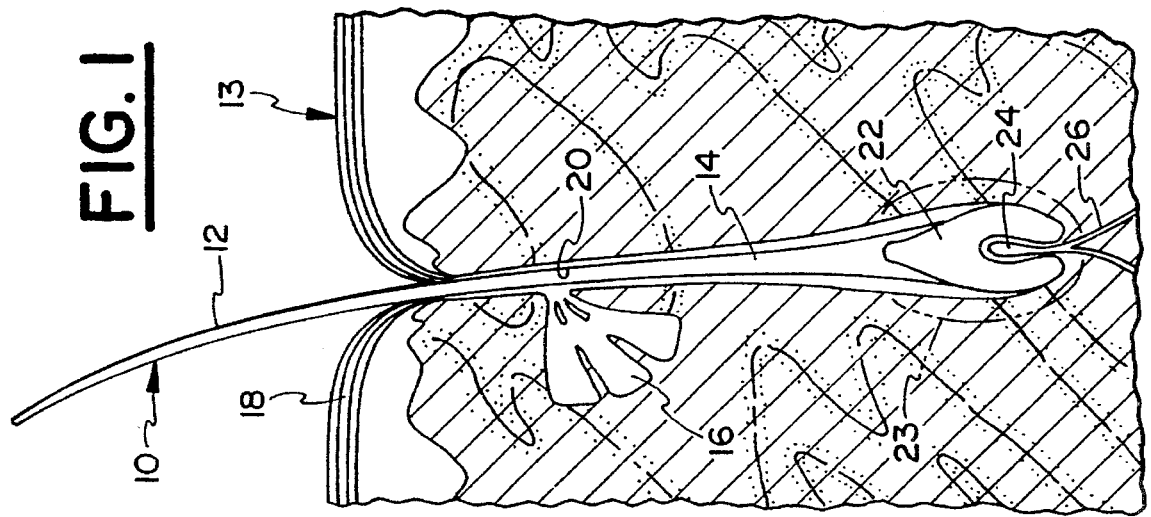

SYSTEM FOR PERMANENT REMOVAL OF MULTIPLE HAIRS

CROSS-REFERENCE TO RELATED APPLICATIONS

This application is a continuation-in-part of application Ser. No. 07/917,662, entitled "Method of Removing Hair from the Body and Inhibiting Future Growth," filed Jul. 20, 1992, abandoned, which is a continuation of application Ser. No. 07/794,364, filed Nov. 13, 1991, abandoned, which is a continuation of Ser. No. 07/454,622, filed Dec. 21, 1989, abandoned, and this application is a continuation-in-part of application Ser. No. 08/066,261, filed May 25, 1993, abandoned, which is a continuation-in-part of application Ser. No. 07/929,750, filed Aug. 17, 1992, abandoned, which is a continuation-in-part of application Ser. No. 07/707,828, filed May 30, 1991, abandoned, and each of which is incorporated herein by reference.

FIELD OF THE INVENTION

This invention relates to a method for removing hair and for permanently impairing future hair growth, and an apparatus for carrying out this method.

BACKGROUND OF THE INVENTION

Inventors have long sought to permanently remove unwanted hair. Known techniques for hair removal are described in patents such as the following.

U.S. Pat. No. 4,174,714 to Mehl discloses a method for permanent removal of hair in which hair is removed and future hair growth is permanently impaired by grasping reduced lengths of a hair between conductive hair engaging surfaces, applying high frequency electrical waves to one of the conductive hair engaging surfaces, and holding the hair engaging surfaces in firm engagement in position against the skin and hair while applying the high frequency electrical waves until the hair releases. Although this method works well, there is a need for an even more efficient method of permanent hair removal.

U.S. Pat. No. 5,026,,369 to Cole discloses a non-invasive method of removing hair through electrolysis in which a particular hair to be removed is cleaned, and then bathed in an electrode solution. A conductor is attached to a remote end of the treated hair after which a DC electrical current is directed down the electrode solution coating outside of the hair to the soft moist tissue surrounding hair within the skin, whereby sodium hydroxide (NaOH) in the hair follicle site is produced owing to the chemical reaction in the presence of electrical current for causing the hair follicle to die and allow the hair associated with the dead hair follicle to be removed.

U.S. Pat. No. 5,049,148 to Mehl discloses a radio frequency hair removal tweezer including tweezer arms having facing interior surfaces including a radio frequency conducting hair engaging metal conducting pad for grasping hair to be removed. Although this hair removal tweezer operates well, there is a need for an effective hair removal method and apparatus which is even simpler and easier to use.

OBJECTS AND SUMMARY OF THE INVENTION

Accordingly, it is an object of the invention to provide a multiple hair removal method and apparatus for carrying out the method that are simpler to perform and to use than the known methods and apparatus.

It is another object of the invention to provide a hair removal method, system, and apparatus suited for removing multiple hairs at one time.

It is a further object of the invention to remove multiple hairs easier and faster without stress and infection.

It is a still further object of the invention to provide a method and apparatus for permanent hair removal and impairment of hair regrowth.

It is an additional object of the invention to provide a hair removal system which has few or no moving parts.

It is a further object of the invention to provide a hair removal system which is simple and which can be used by lay people.

It is yet another object of the invention to provide a method for permanent hair removal that uses an alkaline solution for pretreating the hair in order to more effectively increase the conductivity of hair than is possible with known neutral or acid-based systems.

It is yet another object of the invention to provide a method of permanent hair removal by which an alkaline solution is applied to the hair to be removed for opening the cuticle and cortex layers for causing an electric power source to penetrate the hair easier and faster.

It is a still further object of the invention to provide a method of multiple hair removal by which all treated hairs slide out of their respective treated follicles with substantially no resistance.

It is another object of the invention to provide a permanent multiple hair removal method and apparatus which can be used by both professionals and non-professionals.

It is a yet still further object of the invention to provide a permanent hair removal method and apparatus which make hair removal painless.

It is still another object of the invention to provide a permanent multiple hair removal system which shortens the time required for permanent hair removal.

It is another object of the invention to provide a permanent hair removal system which is less messy than conventional systems.

It is another object of the invention to provide a permanent multiple hair removal system by which skin disorders, such as acne, can be treated concurrently with the hair removal.

It is another object of the invention to provide a permanent multiple hair removal system which uses relatively small, disposable hair removal strips.

It is another object of the invention to provide a permanent hair removal system which uses a protective, non-conductive layer of material directly adjacent the user's skin, in conjunction with a conductor or conductive layer disposed adjacent to the non-conductive layer and spaced apart from the user's skin by the non-conductive layer.

It is yet a still further object of the invention to provide a permanent hair removal system, the components of which can be applied to the user's skin in a liquid form.

It is a further object of the invention to provide a hair removal system that in one instance the hair has to be cut and in another instance left long.

It is another object of the invention to provide a multiple hair removal system which includes a multi-compound liquid which can be stored in a single container prior to use.

It is another object of the invention to provide a hair removal system, the components of which can be used for removing one hair or multiple hairs at a time.

It is a still further object of the invention to provide for multiple hair removal by the application of any one of a number of power sources or by a combination of devices with different power sources.

It is a further object of the invention to provide a substantially painless permanent multiple hair removal method and apparatus, unlike such as associated with traditional wax removal in which live hairs are pulled directly from the skin.

It is a still further object of the invention to provide for permanent multiple hair removal without the need for insertion of an electrolysis needle into the user's skin that causes burns and infection.

It is another object of the invention to provide a multi-purpose conductive pair of tweezers which functions as a conductor to a source of power, as a clamp, as a multiple-hair-removal tweezers, and as a single-hair-removal tweezers.

It is a still further object of the invention to provide for a permanent multiple hair remover system without the need for the single tweezer method which is more time consuming.

These and further objects of the invention will become apparent from the drawings and the following description of the invention.

BRIEF DESCRIPTION OF THE DRAWINGS

FIG. 1 is a schematic cross sectional view of a section of tissue showing a typical hair;

FIG. 2 is a side elevational view of a preferred embodiment of the apparatus according to the invention when in place engaging hairs to be removed;

FIG. 3 is an elevational view similar to FIG. 2 of another preferred embodiment of the apparatus according to the invention;

DETAILED DESCRIPTION OF THE INVENTION

Figure 4:
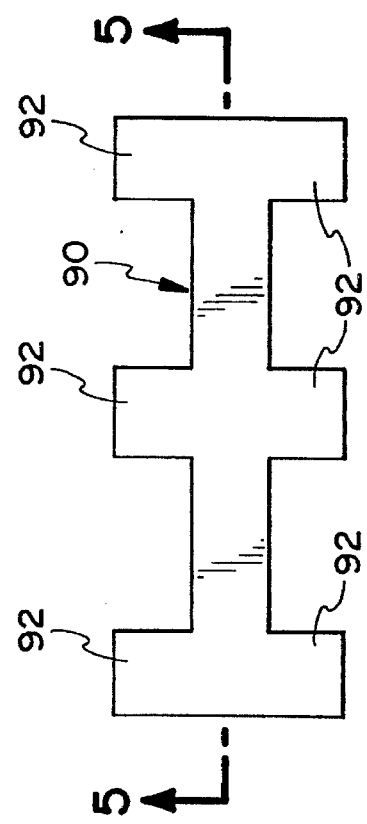
FIG. 4 is a top plan view of a preferred embodiment of a conductive layer of the apparatus according to the invention.

FIG. 1 is a representation of the manner in which hair is typically found. A hair 10 includes an upper shaft portion 12, which extends above a skin surface 13, and an interior lower shaft portion 14 extending beneath skin surface 13. Hair 10 passes adjacent to oil glands 16 disposed immediately below an epidermis area 18. Lower shaft 14 is connected to an external root sheath layer 20. The growth site for hair 10 is located in a matrix area 22. Matrix area 22 contains a papilla 24 supplied with nutrients by a blood vessel 26. Matrix area 22 and the cells 23 surrounding the follicle are the parts which must be reached and destroyed by electrical or chemical energy if future hair growth is to be prevented, given that all of the cells of the hair 10 above matrix area 22 is substantially dead fibrous material.

Accordingly, the target for an electrical current to be applied to hair 10 is essentially papilla 24, matrix area 22, and adjacent cellular structures.

It has been found that substantially dry hair 10 is not a sufficiently good electrical conductor for the present purposes. Hair becomes a better conductor when moisture is allowed to be absorbed into the hair shaft so that an electrical current can be induced. Then electrical current can be conducted from inner upper portion 12 to inner lower shaft portion 14 and, hence, the area around matrix 22.

FIG. 2 shows a preferred embodiment of a multiple hair removal device 50 according to the invention that can carry out the multiple hair removal method according to the invention. Hair removal device 50 includes a non-conductive or conductive glue, adhesive, or wax layer 52, a non-conductive, adhesive, plastic, or wax layer 53, a structural layer 54, and a conductor or conductive layer 56 disposed therebetween. Conductive layer 56 is connected to a power source 70 by means of a power transmission cable 72 or by a clamping means.

Turning to FIG. 3, a still further preferred embodiment of the an apparatus according to the invention is shown as a multiple hair removal device 80. Multiple hair removal device 80 includes a conductive wax, glue, or similar adhesive material defining a conductive layer 82 which includes an adhesive material 84 and electrically conductive material or particles 86 embedded in and dispersed throughout adhesive material 84.

A separate non-conductive layer 85, for placement directly on the skin, is provided in this embodiment.

Adhesive material 84 is selected from compounds which adhere to human hair. Layer 82 is made of conducting material or rendered conductive by the presence of conductive particles 86. An optional structural layer 88 is disposed on top of and adhered to conductive layer 82. Power transmission cable or electrode 72 or clamping means is associated with conductive layer 82 for transmitting power from power source 70.

Figure 5:
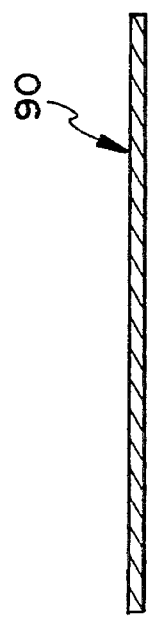
FIG. 5 is a sectional view of the embodiment of FIG. 4, taken along line 5—5.

FIGS. 4 and 5 illustrates a preferred embodiment of a conductive layer 90 for use with the multiple hair removal device such as shown in FIG. 2, when power source 70 is any electrical source. It is expected that an RF (radio frequency) power source be operatively associated with conductive layer 90, for example. Accordingly, RF focusing areas 92 are provided that serve as focal points at which the RF power is intensified. For other electric sources, such as alternating current (AC), direct current (DC), or DC-biased RF (so-called "blend"), the flat configuration pad makes this embodiment a multiple use conductor.

FIG. 5 illustrates that the configuration of RF focusing areas 92 allow for conductive layer 90 to be a substantially flat, foil-like, yet with sharp edges at which the RF is intensified, for example.

Figure 6:
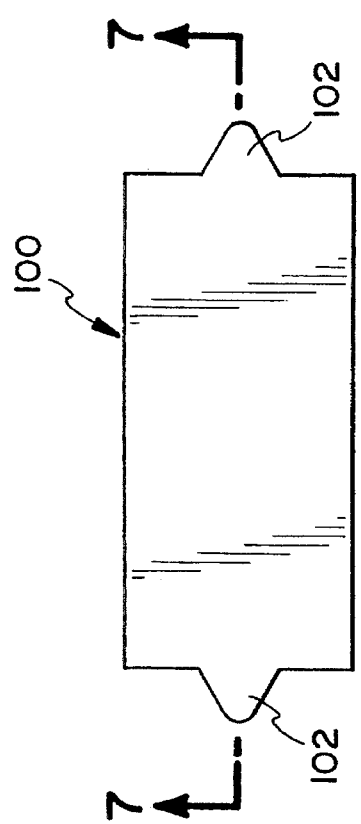
FIG. 6 is a top plan view of another preferred embodiment of the conductive layer of the apparatus according to the invention.
Figure 7:
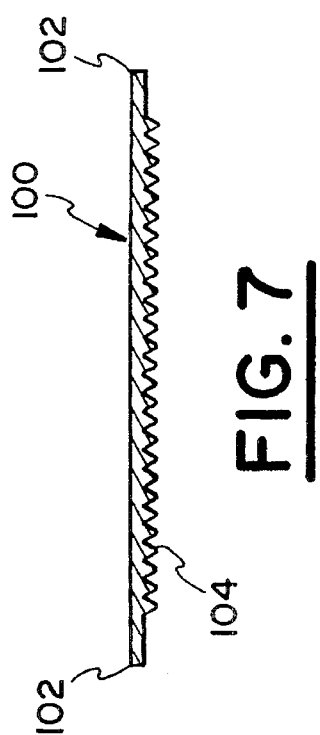
FIG. 7 is a section view of the conductive layer of FIG. 6 taken along line 7—7.

FIGS. 6 and 7 show another preferred embodiment of a conductive layer 100 having attachment tabs 102 that may be used in a multiple hair removal device similar to that shown in the preferred embodiment of FIG. 2. Attachment tabs 102 are used for being attached to a power source by conductive releasable attachment members such as so-called "alligator clips" or tweezers such as described in detail below and shown in FIGS. 13–17. FIG. 7 is a sectional view of FIG. 6 illustrating electrical focusing points 104 which serve as intensifiers and directors for electric power applied to tabs 102. For example, focusing points 104 direct AC or DC, and intensify RF power.

Figure 8:
FIG. 8 is a sectional view similar to FIG. 7, of another preferred embodiment of the conductive layer according to the invention.

FIG. 8 illustrates a still further embodiment of a conductive layer 110 made of a conductive plastic material and which can be used in hair removal device such as shown in FIG. 2.

Figure 11:
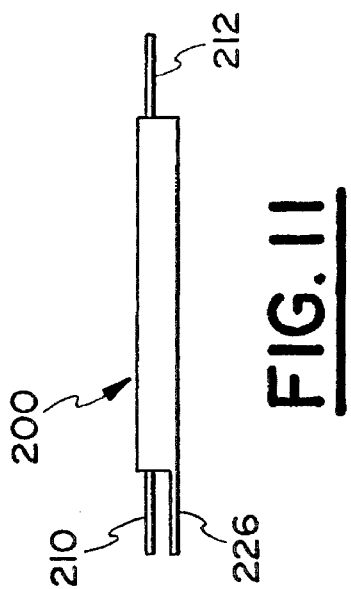
FIG. 11 is a side, elevational view of the preferred embodiment of FIG. 9.
Figure 9:
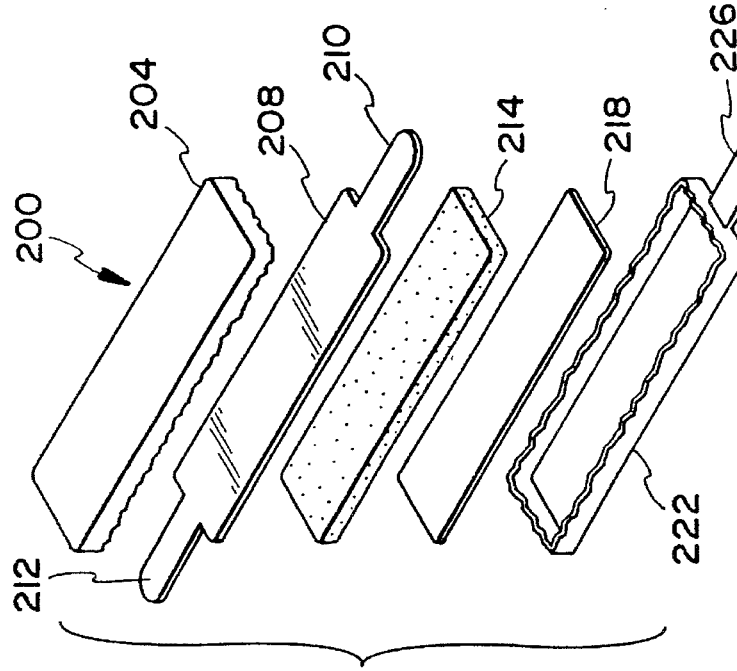
FIG. 9 is a somewhat schematic, exploded view of a still further preferred embodiment of a hair removal device according to the invention.
Figure 10:
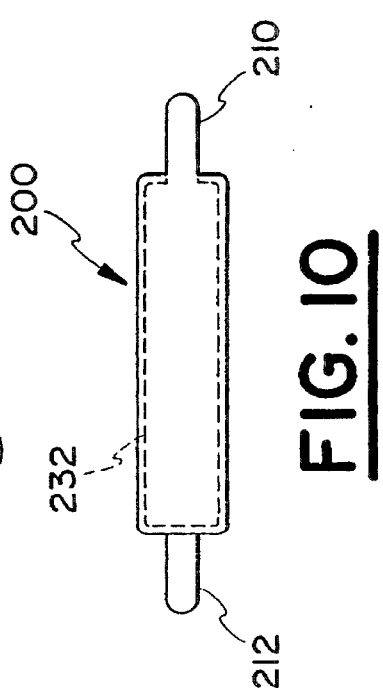
FIG. 10 is a schematic, top plan view of the preferred embodiment of FIG. 9.

Turning to FIGS. 9–11, another preferred embodiment of a hair removal device 200 according to the invention is illustrated. Hair removal device 200 includes a vinyl layer 204, such as a top of an envelope for protecting the operative elements of hair removal device 200 during storage. A conductive layer or conductor 208 includes one or more pull tabs 210, 212, both of which likewise function as conductor leads when in use.

A conductive layer 214 is disposed adjacent conductor 208 and between a non-conductive layer 218 and conductor 208. Non-conductive layer 218 is made of material engineered to removably adhere to the user's skin and to allow hair to penetrate therethrough. A vinyl layer 222 functions as the bottom of a protective envelope including vinyl layer 204, both of which collectively protect conductor 208, conductive layer 214, and non-conductive layer 218 when hair removal device 200 is being stored.

The invention can be carried out with conductor 208, conductive layer 214, and non-conductive layer 218. Still further, it is possible to use just conductive layer 214 and non-conductive layer 218 to achieve the objects of the invention.

As best seen in FIG. 10, a perforation 232 is provided to ensure that vinyl layers 204 and 222 are cleanly separated and removed when one or more of pull tabs 210, 212, and 226 are used.

Figure 12:
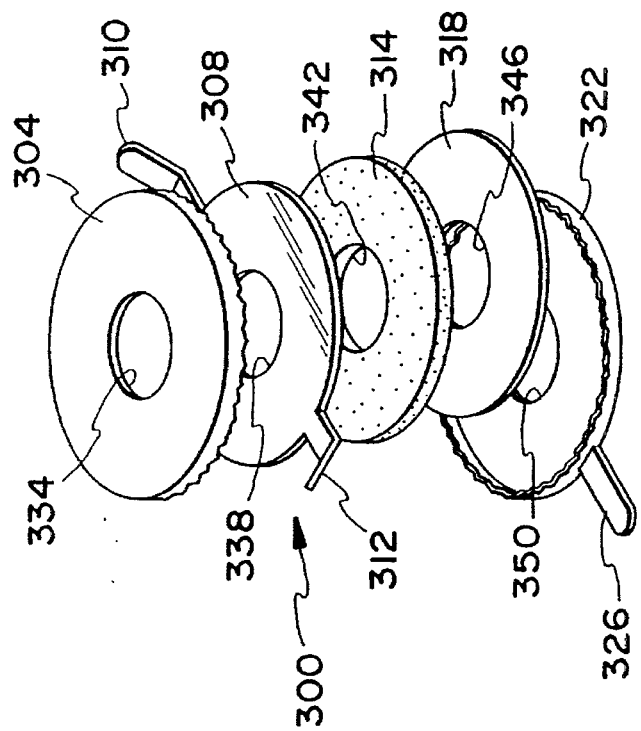
FIG. 12 is a schematic, exploded view of yet another preferred embodiment of a hair removal device according to the invention.

FIG. 12 shows a yet still further embodiment of a hair removal device 300 according to the invention, which has been shown on an exaggerated, exploded view for clarity.

Hair removal device 300 includes a vinyl layer 304 functioning as the top of a protective envelope, a conductor or conductive layer 308 having a pull tab 310 which likewise functions as a conductor lead and, preferably, a second pull tab 312. A conductive layer 314 is disposed between conductor 308 and non-conductive layer 318. A second vinyl layer 322 serves as the bottom of an envelope when joined with top vinyl layer 304, in a manner similar to the embodiment of FIGS. 9–11.

Preferably, a pull tab 326 is provided on vinyl layer 322 for assisting in the separation of vinyl layers 304 and 322 when the hair removal device is to be used.

A hole 334 defined in vinyl layer 304 aligns with an aperture 338 in conductor layer 308, which aperture 308 in turn aligns with a throughhole 342 in conductive layer 314. A further aperture 346 disposed in non-conductive layer 318 is likewise aligned with a hole 350 formed in lower vinyl layer 352. Holes 334 and 350 are optional. This special annular shape is useful when a woman wishes to remove hair around the areola resulting from hormonal changes induced by birth control pills, for example. The respective holes are configured for placement over a woman's nipple to avoid contact with the sensitive skin thereof.

Turning to FIGS. 13–17, various insulated pairs of tweezers or tongs 400 according to additional preferred embodiments of the invention are illustrated.

Figure 13:
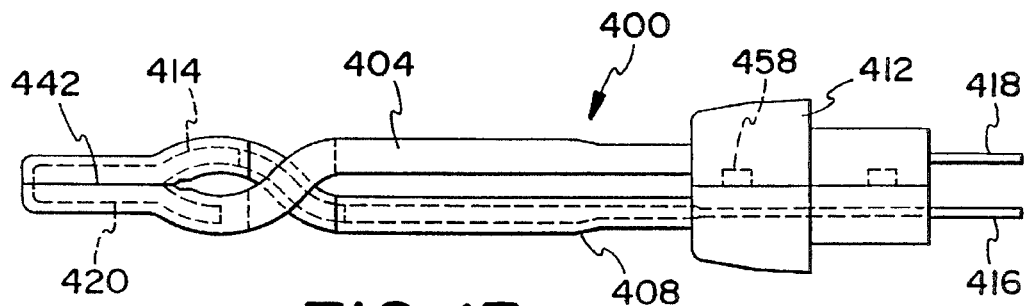
FIG. 13 is a top plan view of a preferred embodiment of conductive tweezers according to a preferred embodiment of the invention.

FIG. 13 shows that insulated tweezers 400 preferably include an upper arm 404 normally biased against a lower arm 408. The terms "upper" and "lower" are used for expedience as the terms describe the relationship of arms 404 and 408 as viewed in FIG. 13, and are not intended to be limiting.

A base 412 is configured for insertion into a casing described below.

A metal insert 414 extends substantially along almost the entire length of lower arm 408 and terminates in a free end or conductive extension 416. An opposed extension 418 can be made of metal or plastic, depending upon the intended use, as will be apparent from the description of the operation of tweezers 400 below.

A conductive metal insert 420 extends along only a part of the length of upper arm 404, as the illustrated pair of tweezers 400 is engineered for use with DC, RF, or DC-biased RF power sources.

Figure 14:
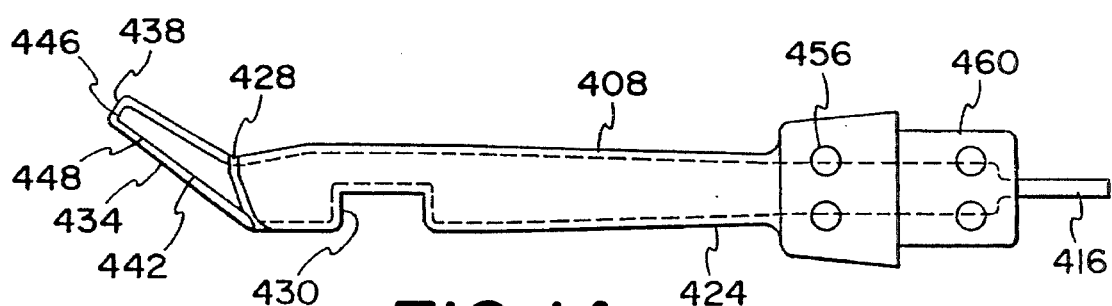
FIG. 14 is a side elevational view of one arm of the pair of tweezers of the preferred embodiment of FIG. 13.

As best seen in FIG. 14, lower arm 408 includes a plastic casing 424 which substantially completely surrounds metal insert 414.

As best seen in FIG. 14 an optional stepped portion 428 of plastic casing 424 demarcates a hair-grasping end 434 of arm 408. A "single" hair grasping free end 438 is defined at an outermost portion of hair-grasping end 434. A hair-contacting portion 442 of metal insert 414 is left partially uncovered by plastic casing 424.

Referring to both FIGS. 13 and 14, one can see that when tweezers 400 are in their normally closed position, hair-contacting portions 442 of opposed tweezer arms 404 and 408 will make contact. In use, hair-contacting portions 442 grasp respective portions of hairs to be treated. Hair-contacting portion 442 has a sufficiently short width at a "single"-hair contacting end 446 that one or two hairs can be conveniently grasped.

A multiple-hair grasping portion 448 of hair-contacting portion 442 is sufficient long that multiple hairs can be grasped at the same time. Single-hair contacting portion 446 is surrounded by insulating material at 438 and elsewhere, so that exposed portion 442 will not contact the user's skin. Likewise, exposed portion 442 is set back from the free edge of insulating plastic casing 424 in the region of multiple-hair contacting region 448 so that the skin is not contacted by exposed portion 442; rather, only the hairs to be treated are grasped and contacted by exposed portion 442.

One or more alignment bosses 456 are provided on lower arm 408 for mating with respective seats 458 disposed in arm 404.

A stepped base portion 460 extends from base 412.

Figure 16:
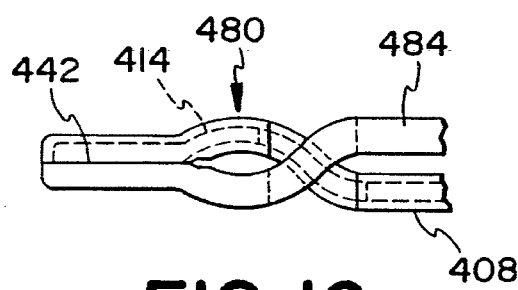
FIG. 16 is a top plan view of still another preferred embodiment of conductive tweezers according to a preferred embodiment of the invention.
Figure 15:
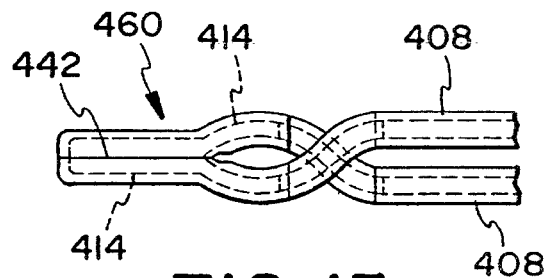
FIG. 15 is a top plan view of another preferred embodiment of conductive tweezers according to a preferred embodiment of the invention.

FIGS. 15 and 16 show additional embodiments, depending on the intended power source and particular application, of insulated tweezers similar to insulated tweezers 400 of FIG. 13. The FIG. 15 tweezers 460 have two opposing arms, each of which have full length conductive metal inserts 414 therein. The FIG. 16 embodiment of a tweezers 480 has two opposing arms, one of which has a full length conductive insert 414, with no metal insert at all in an opposed arm 484; for example.

Figure 17:
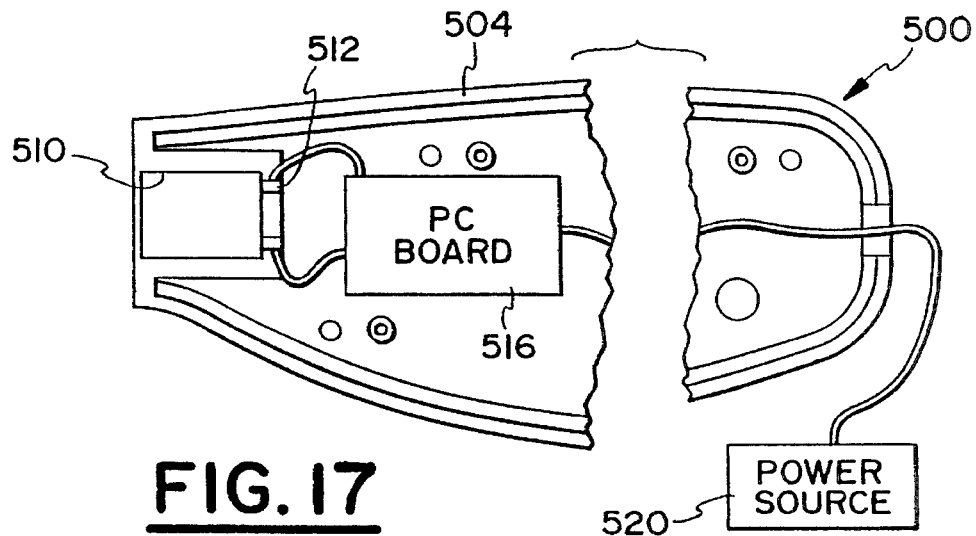
FIG. 17 is a top plan view of one half of a hand-held casing according to a preferred embodiment of the invention suitable for retaining and powering the various pairs of tweezers of the embodiments of FIGS. 13–16.

FIG. 17 illustrates a hand-held casing 500 which is used for securing and powering insulated tweezers 400 of FIGS. 13–16. Hand-held casing 500 includes a plastic case 504 and a tweezers receptacle 510 configured for receiving stepped based portion 460. One or more female connectors 512 receive conductive extension 416 and extension 418. A conventional printed circuit (PC) board 516 converts and regulates the power supplied by a standard power source 520 into the desired type of power used in the hair removal system selected according to the invention, such as AC, DC, DC-biased RF, and the like, as described above.

OPERATION

The preferred embodiment of the method of permanently removing one or more hairs according to the invention will become more apparent by first considering the manner in which the embodiments of the apparatus shown in FIGS. 2–7 are used.

Multiple hair removal device 50 of FIG. 2 is used as follows. Preferably, the skin having hair to be treated and removed is first steamed in order to both open the pores and to moisturize the hair for enhancing conductivity thereof. A conductive solution, which may be a liquid, a gel, an emulsion, or a cream, is applied to the hair. The conductive solution is left in contact with the hair for a predetermined period of time. Preferably, the conductive solution has an alkaline formulation and a pH in the range of about 9 to 11. The length of the predetermined period of time is determined as described below, then the solution is wiped off.

Multiple hair removal device 50 is then pressed against the skin surface to be treated, ensuring that non-conductive adhesive layer 53 is closest to skin surface 13. Upper portion 12 of the hair to be removed extends through non-conductive adhesive layer 53 and contacts adhesive conductive layer 52 as multiple hair removal device 50 is pressed against the skin. Thus, hair 10 itself serves as the path by which power is transmitted from conductive source to matrix root area 22 of the hairs to be destroyed. Some or all of hairs 12 may directly contact conductor 56.

Power source 70 is then turned on for a predetermined length of time. The predetermined period of time is a function of the area of the hair to be treated, the number of hairs to be destroyed, the physical attributes of the hair, the type of power source being used, and like considerations. Accordingly, it is preferred that a preliminary test be done because the length of time required varies not only from person to person, but from one area of the body to another. Advantageously, a test area, commonly known as a "patch test" is done as it serves the additional purpose of determining whether the user is allergic to the conductive solution or to other constituents, such as the adhesive layer and how well the roots and hair accepts the treatment.

After the application of power to kill the hair, the destroyed hair is allowed to remain in the body for a predetermined period of time, inasmuch as a chemical reaction has been started in the vicinity of matrix area 22 by the application of power thereto, and the chemical reaction continues at this site of hair growth for a period of time. This is typically done only with the DC unit.

For a fuller discussion of the chemical processes which are involved, attention is directed to the Mehl '714, Mehl '148, and Cole '369 patents described above, each of which is incorporated herein by reference.

In order to optimize the length of time for which power is applied, one can conduct a test of the removed hairs so as to gauge the amount of destruction of matrix area 22. This is typically done only with DC unit.

This test is accomplished by use of a standard piece of litmus paper and distilled or deionized water. The piece of litmus paper is placed on the test bench, a drop of distilled and/or deionized water is applied, and the matrix area 22 of a removed hair is touched to the surface of the litmus paper. A destroyed matrix area 22 will have undergone a chemical change sufficient that a spot on the piece of litmus paper to which matrix area 22 was touched indicates a pH in the range of about 9 or greater. If the pH registers lower than about 9, then the user simply increases the period of time for which power is applied.

The litmus test is repeated as required to determine the length of time necessary to properly treat a given body area of hair. After the proper length of time for the application of power has been determined, a larger area of the same part of the body can be treated by simply multiplying the length of time the power has been applied to the test area by the ratio of the size of the larger area to be treated to the size of the test area. For example, if one minute was required for properly treating one square inch of hair, then ten minutes would be required for treating ten square inches of the same type of hair.

Preferably, the hair to be removed is substantially uniform and relatively short.

If the hair is not short then it is preferred that the hair be cut in the area to be treated. If it is necessary to shave off the hair, the user's hair should be allowed to grow for about three days so as to achieve a substantially uniform, relatively rigid stubble.

These relatively short and rigid hairs have been found to extend well through non-conductive layer 53 and into conductive adhesive or wax layer 52 for contacting conductive layer 56. This length of hair after about three days growth has likewise been found to ensure that there is sufficient contact area between upper shaft portion 12 of hair 10 and conductive adhesive layer 52 so that the treated hair can be removed.

It is further preferred that in the case of adhesive layer 52 being made of a wax-like substance, layer 52 is pressed in the direction opposite to normal hair growth. After treatment, the hairs having destroyed matrix areas 22 are removed in the opposite direction; namely, in the direction of normal hair growth.

The embodiments of the multiple hair removal device as shown in FIGS. 3–8 are used in a similar fashion. Conveniently, conductive layer 100 of FIG. 6 has tabs 102 to which a readily removable power source can be clamped, for example, as by alligator clips.

Likewise, the embodiments of FIGS. 9–12 are used to remove multiple hairs in a manner similar to the use of the above embodiments.

Tweezers 400 of FIGS. 13 and 14, as well as tweezers 460 and 480 of FIGS. 15 and 16, respectively, are engineered to used in multiple ways.

When using the embodiments of FIGS. 9–12, for example, tweezers 400 serve as power connectors and are attached to conductive pull tabs 210 and 212 in a manner similar to traditional normally closed alligator clips. When tweezers 400 are used to supply power, tweezers 400 can be inserted into hand-held casing 500 by mating extensions 416 and 418 with female connectors 512 as stepped base 460 engages tweezer receptacle 510. Power source 520 then supplies the required power to conductive extension 416, for example, the required power having been determined by PC board 516. The power selected for the particular method is transmitted through metal insert 414 and through exposed portion 442 for supplying power to conductive tabs 210 and 212 of the preferred embodiment of FIG. 9, for example.

If any hairs remain after performing the multiple hair removal treatment methods described above, tweezers 400 and casing 500 of FIGS. 13–15 can be used as a separate operating component of the overall hair removal system. In that case, tweezers 400 will be used to grab single or multiple hairs extending from the user's skin directly after the appropriate steps of applying conductive solutions have been carried out as described above. To open normally closed hair-grasping end 434, the user presses upper arm 404 toward lower arm 408 whereby the arms move relative to each other, facilitated by detent 430. Tweezers 400 are placed against the skin so that hair-grasping end 434 is near to the hairs to be removed. The plastic casing 424 defines the non-conductive regions surrounding exposed metal hair contacting portion 442; namely, a power transmission area is thereby defined.

The preferred sources of power include DC power, radio frequency power, galvanic thermolysis, and combinations thereof, such as DC-biased RF or blend.

The length of time during which the hair is allowed to stay in the body after the power has been treated varies and is preferably about 30 minutes for DC or galvanic method. This time is believed to be adequate for the chemical reaction which has been induced by the application of power at matrix area 22 to continue sufficiently long for the so-called galvanic effect to take place, thereby leading to permanent impairment of future hair growth.

RF, thermolysis, and DC-biased RF or blend treated hairs can be removed immediately after treatment.

The above method effectively removes all treated hairs at this stage of growth. In order to get complete and permanent hair removal, the above method steps will be repeated when the user can see hair stubble in the treated area resulting from hairs at different growth stages not removed by the first treatment. Additional treatments may be required as new hair growth occurs that may be induced by hormonal changes and the user's life cycle.

The preferred materials for the non-conductive and conductive layers include adhesives, glues, and hot or cold waxes, and conductive particles, as required, for conductivity. The conductive layer may be made of conductive metals, conductive plastics, and thin foils of those materials or ceramics.

It is also contemplated that the material of the conductive layer will be selected so that it changes color over time. Thus, exposure to air, exposure to the contacted user's skin (such as by a reaction to the warmth, moisture, and/or pH of the skin), or even exposure to the hair itself will cause a color change in the conductive layer. The color change tells the user useful information such as: the conductive layer material has been on the skin for a sufficient period of time so as to provide a visual indication to the user that the conductive material may be removed, given that the period of time suffices for fully treating the hair to be removed.

It is likewise contemplated that the material of the conductive layer or wax will be selected so that the color of the conductive layer changes as a function of the electric current or other power applied thereto. In that way the user gets visual confirmation that sufficient electrical power and/or electrical power for a sufficiently long period of time has been applied to the conductive material so as to fully treat the hair to be removed.

The configuration of the conductor layer may be changed in order to heighten the effects of a particular power source, provide tabs for attachment to a power source, or to treat specific shapes of the body.

Different sizes of the multiple hair removal devices may be used depending on body area and whether the intended use is for an initial treatment when the removal of large numbers of hairs is required, or smaller devices covering reduced areas of the skin may be used when follow-up treatments are performed or when only a small area of the skin is to be treated. Curved configurations may be used for application to the user's eye brow area or larger square. Round or oblong shapes for arms, legs, or any large area are likewise contemplated.

It is also contemplated that the non-conductive layer of material disposed directly adjacent the user's skin will be supplied in a liquid form which is applied by the user to the area of the user's skin be treated while the material is still liquid. After a period of time, the liquid will dry sufficiently on the user's skin so that a non-conductive semi-solid or solid layer is achieved. Likewise, the conductive layer disposed adjacent the non-conductive layer, and separated from the user's skin by the non-conductive layer, will be applied in a liquid form, and allowed to dry, as necessary. A third layer, such as the conductor layer of some of the preferred embodiments of the invention, will also be applied in liquid form on top of the conductive layer, and be allowed to sufficiently dry, as required.

It is likewise contemplated that the two or more liquid materials described in the previous paragraph will be supplied in a single liquid-retaining container, whereby the user simply shakes the container prior to use, applies all three liquids at the same time by use of an applicator, and the two or three liquid materials separate prior to hardening. In this manner, all the layers will be applied at once in a liquid form with only one liquid application step.

In the case of two or three liquids in one container, the liquids will preferably be immiscible, and the lowermost, non-conductive material will be heaviest, so that it sinks to the lowermost point and, in use, contacts the skin.

While this invention has been described as having a preferred designs, it is understood that it is capable of further modifications, uses and/or adaptations of the invention following in general the principle of the invention and including such departures from the present disclosure as come within the known or customary practice in the art to which to invention pertains and as may be applied to the central features hereinbefore set forth, and fall within the scope of the invention and of the limits of the appended claims.

What is claimed is:

1. A hair removal system comprising:

a) a structural layer;

b) an electrically conductive adhesive layer disposed on said structural layer, said electrically conductive adhesive layer including:

i) an adhesive material, said adhesive material being sufficiently strong for adhering to and removing a plurality of treated hairs from skin; and ii) a plurality of conductive particles disposed in said adhesive material; and c) a non-conductive adhesive layer disposed on said conductive layer, and said non-conductive adhesive layer is configured to lay against skin, and to allow hair to project therethrough, and to protect a user's skin from shock and burns when in use.

2. A hair removal system as defined in claim 1, wherein:

a) said electrically conductive adhesive layer includes a cold wax material.

3. A hair removal system as defined in claim 1, wherein:

a) said electrically conductive adhesive layer includes a hot wax material.

4. A hair removal system as defined in claim 1, wherein:

a) a separate conductor is disposed on said electrically conductive adhesive layer.

5. A hair removal system as defined in claim 4, wherein:

a) said separate conductor includes a liquid material.

6. A hair removal system as defined in claim 1, wherein:

a) said electrically conductive adhesive layer includes a conductive plastic material.

7. A hair removal system as defined in claim 1, wherein:

a) an electrode is attached to said electrically conductive adhesive layer.

8. A hair removal system as defined in claim 7, wherein:

a) said electrode is detachably attached to said electrically conductive adhesive layer.

9. A hair removal system as defined in claim 1, wherein:

a) said electrically conductive adhesive layer includes a liquid material.

10. A hair removal system as defined in claim 1, wherein:

a) said non-conductive adhesive layer includes a liquid material.

11. A hair removal system as defined in claim 1, wherein:

a) said non-conductive adhesive layer includes a cold wax material.

12. A hair removal system as defined in claim 1, wherein:

a) said non-conductive adhesive layer includes a hot wax material.

\* \* \* \* \*